United States Patent
Punja

[11] 3,979,519
[45] Sept. 7, 1976

[54] INSECTICIDAL ESTERS
[75] Inventor: Nazim Punja, Wokingham, England
[73] Assignee: Imperial Chemical Industries Limited, London, England
[22] Filed: Dec. 5, 1975
[21] Appl. No.: 638,282

[30] Foreign Application Priority Data
Dec. 5, 1974 United Kingdom............... 52602/74

[52] U.S. Cl. .......................... 424/304; 260/465 F; 260/465 D; 260/468 H; 260/514 H; 260/544 L; 260/612 D; 260/613 D; 424/305; 424/306
[51] Int. Cl.² ...................... A01N 9/20; A01N 9/24; C07C 69/74; C07C 121/75
[58] Field of Search .................... 260/465 D, 468 H; 424/304, 305

[56] References Cited
UNITED STATES PATENTS
3,792,079 2/1974 D'Orazio et al. ............... 260/468 H
3,795,696 3/1974 Ratsuda et al. ................. 260/468 H Primary Examiner—Lewis Gotts
Assistant Examiner—Dolph H. Torrence
Attorney, Agent, or Firm—Cushman, Darby & Cushman

[57] ABSTRACT

Compounds of the formula

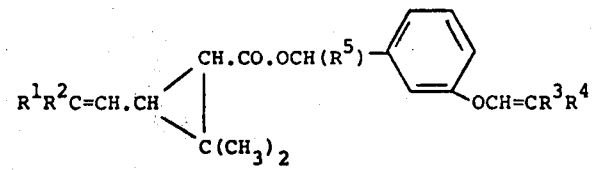

wherein $R^1$ and $R^2$ represent halogen radicals or lower alkyl groups; $R^3$ and $R^4$ represent halogen radicals; and $R^5$ represents a hydrogen atom or the cyano radical. These compounds are effective against insect pests.

14 Claims, No Drawings

INSECTICIDAL ESTERS

This invention relates to novel esters, to processes for preparing them, to compositions comprising them, and to methods of combating insect pests using them.

Accordingly the present invention provides esters of formula:

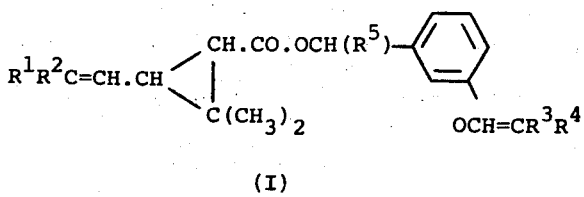

(I)

wherein $R^1$ and $R^2$ represent halogen radicals or lower alkyl groups; $R^3$ and $R^4$ represent halogen radicals; and $R^5$ represents a hydrogen atom or the cyano radical.

By the term "halogen" as used herein is meant fluorine, chlorine or bromine; and by the term lower alkyl group is meant an alkyl group containing up to four carbon atoms.

In a preferred form the invention provides compounds wherein $R^1$ and $R^2$ are both methyl groups, or both chlorine radicals, or both bromine radicals. An especially preferred group of compounds within the invention are those wherein $R^1$, $R^2$, $R^3$ and $R^4$ are all chlorine radicals.

It will be readily appreciated that the compounds of the invention as set out hereinabove are described without reference to their stereochemical nature. Thus the above formula does not differentiate between the cis and trans geometrical isomers which are possible due to the substitution pattern around the cyclopropane ring, nor does it differentiate between the various stereoisomeric forms which may be present, and the present invention includes within its scope all such geometric and optical stereoisomers. Thus the term "compound" as used herein in relation to esters of the invention refers both to an individual isomer in isolation, and to mixtures of isomers thereof e.g. racemic mixtures, diastereoisomeric mixtures.

The following compounds are typical examples of compounds according to the invention.

3(2,2-dichlorovinyloxy)benzyl (±) cis/trans-chrysanthemate (hereinafter referred to as Compound 1).

3(2,2-dichlorovinyloxy)benzyl (±) cis/trans-2(2,2-dichlorovinyl)3,3-dimethylcyclopropane carboxylate (hereinafter referred to as Compound 2).

3(2,2-dichlorovinyloxy)benzyl (±) cis-2(2,2-dichlorovinyl)-3,3-dimethylcyclopropane carboxylate (hereinafter referred to as Compound 3).

3(2,2-dichlorovinyloxy)benzyl (±) trans-2(2,2-dichlorovinyl)-3,3-dimethylcyclopropane carboxylate (hereinafter referred to as Compound 4).

(±)α-cyano-3(2,2-dichlorovinyloxy)benzyl (±) cis/trans-2(2,2-dichlorovinyl)3,3-dimethylcyclopropane carboxylate (hereinafter referred to as Compound 5).

(±)α-cyano-3(2,2-dichlorovinyloxy)benzyl (±) cis-2(2,2-dichlorovinyl)3,3-dimethylcyclopropane carboxylate.

(−)α-cyano-3(2,2-dichlorovinyloxy)benzyl (+) cis-2(2,2-dichlorovinyl)3,3-dimethylcyclopropane carboxylate.

3(2,2-dichlorovinyloxy)benzyl (±) cis/trans-2(2,2-dibromovinyl)3,3-dimethylcyclopropane carboxylate.

3(2,2-dibromovinyloxy)benzyl (±) cis/trans-chrysanthemate.

3(2,2-dibromovinyloxy)benzyl (±) cis/trans-2(2,2-dichlorovinyl)3,3-dimethylcyclopropane carboxylate.

(±)α-cyano-3(2,2-dichlorovinyloxy)benzyl (±) cis/-transchrysanthemate.

(±)α-cyano-3(2,2-dichlorovinyloxy)benzyl (±) cis/-trans-2(2,2-dibromovinyl)3,3-dimethylcyclopropane carboxylate.

The invention compounds may be prepared by several different processes. Thus a compound of formula:

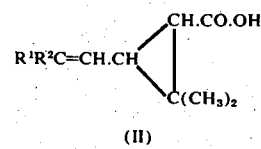

(II)

optionally in the form of a metal salt thereof, may be reacted with a compound of formula:

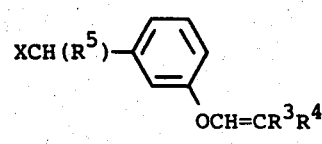

(III)

wherein X is a halogen atom, preferably a chlorine or bromine atom, and $R^1$, $R^2$, $R^3$, $R^4$ and $R^5$ have any of the meanings given hereinabove. Alternatively a compound of formula:

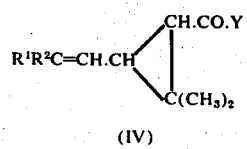

(IV)

may be reacted with a compound of formula:

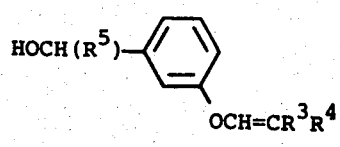

(V)

wherein Y is a halogen atom, preferably a chlorine atom, and $R^1$, $R^2$, $R^3$, $R^4$ and $R^5$ have any of the meanings given hereinbefore.

In another process the invention esters may be obtained by the process of transesterification wherein the mixture of a simple ester (e.g. a lower alkyl ester such as the methyl or ethyl ester) of the acid of formula II and the alcohol of formula V is heated in a solvent or diluent, preferably in the presence of a base (e.g. a lower alkoxide such as sodium methoxide or ethoxide).

These processes may in some cases be carried out by heating the reactants together in the absence of a diluent and/or a base, but preferably a solvent or diluent and a base is present. Suitable solvents include, for example, non-hydroxylic materials such as aliphatic ketones (e.g. acetone), dimethylformamide, dimethylsulphoxide, sulpholane, acetonitrile and tetrahydrofuran. Of these an aliphatic ketone such as, for example acetone is particularly preferred. Hydroxylated solvents, for example, methanol and ethanol, may be used in certain circumstances when the presence of the hydroxyl group does not interfere with the progress of the reaction. Suitable bases include sodium hydride (although not when a hydroxylated solvent or diluent is used), alkali metal carbonates, such as potassium carbonate and alkali metal hydroxides such as potassium hydroxide. The temperature at which the reaction may be carried out will depend upon the choice of reactants, solvent or diluent and base. When acetone and potassium carbonate are used the reaction generally takes place at the ambient temperature. Higher temperatures, up to 100°C, may be employed when other bases are employed. A typical process consists of dissolving or suspending the reactants in a solvent in the presence of a base. After allowing a period of time for the reaction to occur the product may be isolated by the removal of any insoluble portion by filtration and evaporation of the filtrate. The product may be purified by distillation under reduced pressure, or by a suitable chromatographic technique. When it is desired to produce a single geometrically isomeric form of an invention ester this may be achieved either by using a pure cis or trans acid or acid derivative of formula II or III above, or by using a cis/trans mixture thereof and separating the required isomer from the mixture of esters produced by for example a chromatographic technique.

The compounds of formula III and formula V which are used in the above processes for the preparation of the invention esters are themselves novel compounds, and may be prepared by the following processes.

Thus a compound of formula III wherein $R^5$ is hydrogen may be prepared from a compound of the formula:

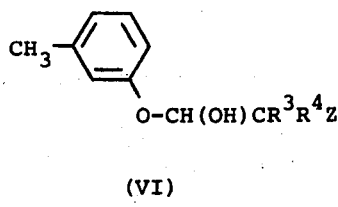

(VI)

by subjecting them to chemical or electrochemical reductive dehydrohalogenation to give a compound of formula:

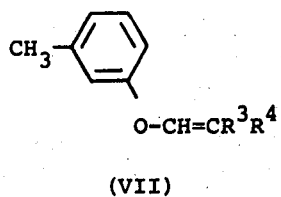

(VII)

and thereafter halogenating the methyl group of compound VII to produce the required compound of formula III. Z in formula VI is a halogen radical, and is preferably the same halogen radical as that represented by $R^3$ and $R^4$.

Compounds of formula VI may be prepared by a method analogous to that of von Hesse and Moll, J. Prakt. Chemie, 1974, 316(2), 304 in which anhydrous chloral or bromal is reacted with m-cresol in the presence of an acyl halide.

The electrochemical reduction procedure may be carried out in organic solvents, for example lower alcohols, such as methanol or ethanol, cyclic ethers such as dioxan or tetrahydrofuran, aliphatic ketones such as acetone or cyclohexanone, or mixtures of these solvents with water or water containing strong mineral acids such as sulphuric, hydrochloric or phosphoric acids.

The reduction is believed to occur principally at the cathode with a high hydrogen overvoltage, for example a mercury, lead amalgam or lead cathode. The reaction can be conveniently carried out in a cell fitted with a ceramic or glass fritted diaphragm, a stirrer, a working electrode and a reference electrode. The process may be adapted for continuous production of the required product by use of a solvent system with which the product of the reaction may be extracted, for example methylene chloride.

The metallic reductive dehydrohalogenation may be carried out with a suitable reducing medium such as zinc dust and acetic acid.

Halogenation of the compounds of formula VII may conveniently be carried out with the aid of a source of positive halogen, for example an N-haloimide such as N-bromosuccinimide, or N-chlorosuccinimide. The compounds of formula V wherein $R^5$ is hydrogen may conveniently be prepared from the corresponding compounds of formula III by, for example, treating them with an alkali metal hydroxde, or alternatively converting them to the corresponding tosylate (p-toluenesulphonate) and subjecting the tosylate to hydrolysis.

Compounds of formula III wherein $R^5$ is hydrogen may be converted to the corresponding compounds wherein $R^5$ is a cyano radical by the process of treating a compound of formula III wherein $R^5$ is hydrogen with a source of cyanide ion, e.g. an alkali metal cyanide such as sodium cyanide, and thereafter subjecting the compound of formula:

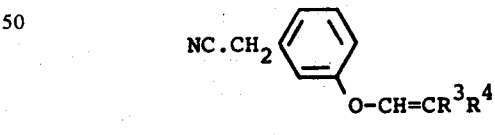

(VIII)

thus produced to further halogenation. The reaction with cyanide may conveniently be performed in a polar aprotic solvent such as dimethylformamide, at an elevated temperature in the range 50° to 100°C. The halogenation step may conveniently be performed in the manner outlined above for the preparation of compound of formula III wherein $R^5$ is hydrogen. The compounds of formula V wherein $R^5$ is cyano may be obtained from the compounds of formula III where $R^5$ is cyano by analogous processes to those set out above for the corresponding compounds where $R^5$ is hydrogen.

A preferred method for the preparation of compounds of formula V where $R^5$ is cyano is however based on a different approach in which a compound of formula VII is selectively oxidised to a compound of formula:

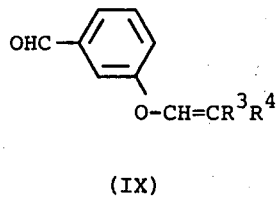

(IX)

and this compound is then converted to its cyanohydrin by reaction with hydrogen cyanide, or, preferably, via the bisulphite compound, with cyanide ion (e.g. sodium cyanide). An alternative process for preparing compound IX involves the oxidation of compound V where $R^5$ is hydrogen with aluminium isopropoxide and acetone under the conditions of the Oppenauer reaction.

In another aspect therefore the invention provides compounds of formula III, V, VII, VIII and IX, all useful as intermediates in the preparation of the invention esters of formula I, and processes for the preparation of the said compounds of formula III, V, VII, VIII and IX.

As stated above the invention esters of formula I are useful as insecticides, and are most conveniently used as such when formulated into compositions. In another aspect therefore the invention provides insecticidal compositions which comprise as an active ingredient an invention ester of formula I in association with agriculturally and horticulturally acceptable diluent or carrier materials.

In a preferment of this aspect of the invention the active ingredient is selected from amongst the specifically named esters of the invention set out hereinabove.

The compositions are for use in agriculture or horticulture but the type of composition used in any instance will depend upon the particular purpose for which it is to be used.

The compositions may be in the form of granules or powders comprising the active ingredient and a solid diluent or carrier. The compositions may also be in the form of liquid preparations to be used as dips or sprays which are generally aqueous dispersions or emulsions.

The compositions to be used as sprays may also be in the form of aerosols wherein the formulation is held in a container under pressure in the presence of a propellant such as fluorotrichloromethane or dichlorodifluoromethane.

For agricultural or horticultural purposes, an aqueous preparation containing between 0.0001% and 1.0% by weight of the active ingredient or ingredients may be used.

The compositions of the present invention may, if desired, also comprise in addition to a compound of the present invention, at least one other biologically active ingredient, for example, an insecticide or a fungicide. They may also comprise a synergist of the type useful in synergising the activity of pyrethroids type insecticides.

In use, the invention compounds or compositions may be used to combat insects in a variety of ways. Thus the insects themselves, or the locus of the insects or the habitat of the insects is treated with a compound or a composition according to the invention.

The invention also provides a method of treating plants to render them less susceptible to damage by insects, which comprises treating the plants, or the seeds, corms, bulbs, tubers, rhizomes or other propagative parts of the plants, or the medium in which the plants are growing with a compound or composition according to the invention.

Thus the compounds of the invention are toxic towards a wide variety of insect and other invertebrate pests, including for example the following:

| | |
|---|---|
| Tetranychus telarius | Blatella germanica |
| Aphis fabae | Musca domestica |
| Megoura viceae | Pieris brassicae |
| Aedes aegypti | Plutella maculipennis |

The invention is illustrated by the following Examples.

EXAMPLE 1

This Example illustrates the preparation of Compound no. 1.

A mixture of dl-chrysanthemic acid (50:50, cis:trans; 1.2 g), 3(2,2-dichlorovinyloxy)benzyl bromide (2.0 g), anhydrous potassium carbonate (1.0 g) and acetone (25 ml) was stirred at the ambient temperature (ca. 18°–22°C) for 18 hours. The insoluble portion was removed by filtration and the filtrate evaporated under reduced pressure to yield a residual oil which was dissolved in chloroform and washed with saturated sodium bicarbonate solution and then with water. After drying the chloroform solution over anhydrous magnesium sulphate the solvent was removed under reduced pressure and the residual oil subjected to preparative thin layer chromatography using a mixture of chloroform (10% v/v) and petroleum ether (boiling range 40°–60°C; 90% v/v) as eluent. The required product was identified by infra-red and nuclear magnetic spectroscopy.

EXAMPLE 2

This Example illustrates the preparation of Compound no. 2.

A mixture of dl-3(2,2-dichlorovinyl)2,2-dimethylcyclopropane carboxylic acid (80:20, trans:cis; 0.75 g), 3(2,2-dichlorovinyloxy)benzyl bromide (1.0 g), anhydrous potassium carbonate (0.5 g) and acetone (25 ml) was stirred at the ambient temperature for 18 hours. The product was isolated from the reaction mixture by a procedure similar to that used in Example 1, except that diethyl ether was used in place of chloroform as solvent, and the T.L.C. eluent consisted of 20% v/v chloroform and 80% v/v petroleum ether (boiling range 40°–60°C).

EXAMPLE 3

This Example illustrates the preparation of (±) α-cyano-3(2,2-dichlorovinyloxy)benzyl (±) cis/trans-2(2,2-dichlorovinyl)3,3-dimethylcyclopropane carboxylate, Compound no. 5, (Formula I; $R^1$, $R^2$, $R^3$, $R^4$ are chlorine radicals, $R^5$ is a cyano radical).

2(2,2-Dichlorovinyl)3,3-dimethylcyclopropane carboxylic acid (cis/trans (40:60, 1.29 g) is added to thionyl chloride (5.0 g) and the mixture heated at 100°C (steam bath) for one hour, after which the excess thionyl chloride is removed by azeotropic distillation with toluene. The residual acid chloride thus produced is dissolved in n-hexane (3.0 ml) and the solution obtained added dropwise at the ambient temperature to a solution of 3(2,2-dichlorovinyloxy) benzaldehyde cyanohydrin (1.5 g) in a mixture of n-hexane (7.0 ml) and pyridine (0.5 ml). After completing the addition the mixture is stirred for two hours at the ambient temperature. The solid precipitate which forms is then removed by filtration and the filtrate washed with water (2 × 10 ml), dried over anhydrous magnesium sulphate and concentrated by evaporation of the solvent under reduced pressure. The residual oil is subjected to preparative thin layer chromatography using silica plates and as eluent a mixture of chloroform (2 parts by volume) and petroleum ether (boiling range 60°–80°C, 3 parts by volume), to yield substantially pure (±) α-cyano-3(2,2-dichlorovinyloxy)benzyl (±) cis/trans-2(2,2-dichlorovinyl)3,3-dimethylcyclopropane carboxylate, consisting of 40% of the cis isomer and 60% of the trans isomer.

EXAMPLE 4

This Example illustrates the preparation of Compounds Nos. 3 and 4.

The product obtained by the process of Example 2 (250 mg) was subjected to preparative thin layer chromatography using a silica coated plate and a solvent mixture comprising 35% v/v chloroform - 65% v/v petroleum ether (60°–80°C). The required products were identified by infra-red and nuclear magnetic spectroscopy as Compound 3 (70 mg; (±) cis-isomer) and Compound 4 (100 mg; (±) trans-isomer).

EXAMPLE 5

This Example illustrates the preparation of 3(2,2-dichlorovinyloxy)benzyl bromide.

a. Preparation of 1(3-tolyloxy)-2,2,2-trichloroethyl acetate.

To a solution of anhydrous chloral (37.0 g) in dry ether (125 ml) was added meta-cresol (27.0 g) and the mixture was stirred at the ambient temperature for 20 minutes, after which it was cooled to 10°C and a solution of triethylamine (25.25 g) in dry ether (100 ml) was slowly added. Acetyl chloride (20.0 g) was then carefully added to the stirred mixture and stirring was continued for one hour. The insoluble material was removed by filtration and the filtrate dried over anhydrous magnesium sulphate. After removal of the ether by evaporation under reduced pressure the residual oil was distilled under high vacuum and the fraction boiling at 132°–134°/0.5 mm Hg collected. Infra-red and nuclear magnetic spectroscopic analysis indicated that this was 1(3-tolyloxy)-2,2,2-trichloroethyl acetate.

b. Preparation of 3-tolyl 2,2-dichlorovinyl ether.

i. By a metallic reductive dehydrohydrogenation method. 1(3-tolyloxy)-2,2,2-trichloroethyl acetate (14.2 g) was dissolved in glacial acetic acid (40 ml) and zinc dust (3.6 g) was slowly added to the solution with stirring at the ambient temperature. The temperature rose to 60°C in response to the exothermic reaction which occurred, after which the mixture was heated at 50°–60°C for 4 hours. The mixture was filtered and the filtrate poured in an excess of water and extracted with chloroform. The extracts were washed twice with water, with saturated sodium bicarbonate solution, and finally with water. After drying the chloroform extracts over anhydrous magnesium-sulphate, the solvent was removed by evaporation under reduced pressure and the residual oil distilled to yield crude 3-tolyl 2,2-dichlorovinyl ether, collected as a fraction boiling at 92°–95°C/0.3 mm, which was redistilled and the fraction boiling at 84°C/0.2 mm Hg collected.

ii. By an electrochemical reductive dehydrohalogenation method 1(3-tolyloxy)-2,2,2-trichloroethyl acetate (15.8 g), concentrated sulphuric acid (98% w/v, 9.8 g) and methanol (220 ml) was charged into an electrolytic cell, which was surrounded by a cooling bath set to maintain the temperature at about 15°C, and fitted with a cylindrical diaphragm, stirrer, reference electrode (SCE) and a working electrode. The cathode was a lead plate (surface area about 40 cm$^2$). Using a current density in the range 5 to 10 mA/cm$^2$ the reaction was conducted in the potential range −1100 to 1700 mV (SCE). When reduction was completed the cathodic electrolyte was neutralised with caustic soda and extracted with methylene chloride, the extracts dried over anhydrous sodium sulphate and evaporated to yield a residue of crude 3-tolyl 2,2-dichlorovinyl ether.

c. Preparation of 3(2,2-dichlorovinyloxy)benzyl bromide.

3-Tolyl 2,2-dichlorovinyl ether (12.2 g) was dissolved in carbon tetrachloride (75 ml), and N-bromosuccinimide (12.0 g) and a trace of wet benzoyl peroxide added, and the mixture refluxed for 3 hours. After filtration the solvent was evaporated from the filtrate, and the residue dissolved in ether and extracted with 1% w/v sodium hydroxide solution. The ethereal solution was dried over anhydrous magnesium sulphate, the solvent removed by evaporation under reduced pressure, and the residual oil distilled to yield a fraction boiling at 150°C/0.5 mm Hg. This fraction was shown by NMR to contain about 65% of the required product together with about 30% of unchanged starting material, the remainder being a small proportion of the dibromomethyl compound.

EXAMPLE 6

This example illustrates the preparation of 3(2,2-dichlorovinyloxy)benzyl alcohol.

A mixture 3(2,2-dichlorovinyloxy)benzyl bromide (2.8 g), sodium p-toluene sulphonate (2.0 g) and methanol (20 ml) is warmed to 50°C for 1 hour, after which water (20 ml) and toluene (20 ml) is added with agitation. The toluene layer is separated, washed with water and concentrated by evaporation of the solvent under reduced pressure. The concentrate is then added dropwise to a 15% (w/v) aqueous solution of potassium hydroxide (100 ml) and the mixture warmed to 60°C for 1 hour, cooled to the ambient temperature and extracted with a mixture of toluene (10 ml) and methyl iso-butylketone (10 ml), the extracts dried over anhydrous magnesium sulphate and the solvents evaporated under reduced pressure to yield 3(2,2-dichlorovinyloxy)benzyl alcohol as a residual pale yellow oil.

EXAMPLE 7

This Example illustrates the conversion of 3(2,2-dichlorovinyloxy)benzaldehyde to its cyanohydrin, via the bisulphite compound.

To a stirred solution of sodium metabisulphite (3.2 g) in a mixture of water (5.2 ml) and methanol (5.2 ml) at the ambient temperature is added 3(2,2-dichlorovinyloxy) benzaldehyde (2.0 g). After 30 minutes the white precipitate which forms is collected by filtration, washed with cold methanol and dried to yield the bisulphite compound of 3(2,2-dichlorovinyloxy)-benzaldehyde (2.5 g). This is suspended in water (5 ml) and to it is added a solution of sodium cyanide (0.4 g) in water (5 ml) at the ambient temperature. The mixture is stirred for 2 hours and then extracted with diethyl ether (2 × 10 ml). The extracts are combined, washed with water (2 × 10 ml), dried over an hydrous magnesium sulphate and evaporated under reduced pressure to yield the cyanohydrin of 3(2,2-dichlorovinyloxy)-benzaldehyde as a yellow oil.

A dash (—) in Table I indicates that no test was carried out.

In Table I 'contact test' indicates that both the pests and the medium were treated and 'residual test' indicates that the medium was treated before infestation with the pests.

TABLE I

| PEST SPECIES | SUPPORT MEDIUM | NO. OF DAYS | COMPOUND NO. 1 2 3 4 5 |
|---|---|---|---|
| Tetranychus telarius (red spider mites, adults) | French Bean | 3 | 1 0 0 1 — |
| Aphis fabae (black aphids) | Broad Bean | 2 | 3 3 2 0 0 |
| Megoura viceae (green aphids) | Broad Bean | 2 | 0 3 3 3 2 |
| Aedes aegypti (mosquito adults) | Plywood | 1 | 2 2 3 3 2 |
| Musca domestica (houseflies - contact test*) | Milk/ sugar | 2 | 3 3 3 2 3 |
| Plutella maculipennis (diamond back moth, larvae) - contact test | Mustard | 2 | 0 3 3 2 3 |
| Pieris brassicae (cabbage white caterpillars - contact test) | Cabbage | 2 | 3 3 3 3 3 |
| Musca domestica (houseflies - residual test*) | Plywood | 2 | 0 3 3 3 3 |

EXAMPLE 8

The activity of a number of the compounds was tested against a variety of insect and other invertebrate pests. The compounds were used in the form of a liquid preparation containing 0.1% by weight of the compound except in the tests with *Aedes aegypti* where the preparations contained 0.01% by weight of the compound. The preparations were made by dissolving each of the compounds in a mixture of solvents consisting of 4 parts by volume of acetone and 1 part by volume of diacetone alcohol. The solutions were then diluted with water containing 0.01% by weight of a wetting agent sold under the trade name "LISSAPOL" NX until the liquid preparations contained the required concentration of the compound. "Lissapol" is a Trade Mark.

The test procedure adopted with regard to each pest was basically the same and comprised supporting a number of the pests on a medium which was usually a host plant or a foodstuff on which the pests feed, and treating either or both the pests and the medium with the preparations.

The mortality of the pests was then assessed at periods usually varying from one to three days after the treatment.

The results of the tests are given below in Table I. In this table the first column indicates the name of the pest species. Each of the subsequent columns indicates the host plant or medium on which it was supported, the number of days which were allowed to elapse after the treatment before assessing the mortality of the pests, and the results obtained for each of the compounds numbered as above. The assessment is expressed in integers which range from 0–3.

0 represents less than 30% kill
1 represents 30 – 49% kill
2 represents 50 – 90% kill
3 represents over 90% kill

EXAMPLE 9

This Example illustrates a dusting powder which may be applied directly to plants or other surfaces and comprises 1% by weight of Compound no. 1 and 99% by weight of talc.

EXAMPLE 10

25 Parts by weight of Compound no. 2, 65 parts by weight of xylene and 10 parts of an alkyl aryl polyether alcohol ('Triton' X-100; 'Triton' is a Trade Mark) were mixed in a suitable mixer. There was thus obtained an emulsion concentrate which can be mixed with water to produce an emulsion suitable for use in agricultural applications.

EXAMPLE 11

10 Parts by weight of Compound no. 2, 10 parts of an ethylene oxide-octylphenol condensate ('Lissapol' NX; 'Lissapol' is a Trade Mark) and 80 parts by weight of diacetone alcohol were thoroughly mixed. There was thus obtained a concentrate which, on mixing with water, gave an aqueous dispersion suitable for application as a spray in the control of insect pests. "LISSAPOL" NX is a condensate of 1 mole of nonyl phenol with 8 moles of ethylene oxide.

EXAMPLE 12

This Example illustrates the preparation of 3(2,2-dichlorovinyloxy)benzaldehyde.

3(2,2-Dichlorovinyloxy)benzyl bromide (2.5 g) was carefully added to a stirred solution of hexamethylene tetramine (2.1 g) in carbon tetrachloride (20 ml) at the ambient temperature. After five minutes the precipitate was collected by filtration and washed with acetone. The solid thus obtained was added to aqueous acetic acid solution (50% by weight, 16 ml) and the mixture refluxed for one hour. A mixture of water (16 ml) and concentrated hydrochloric acid (4.5 ml) was then added and the mixture refluxed for a further 15 minutes. After cooling the mixture was extracted with chloroform, the extracts washed with water (twice), dried over anhydrous magnesium sulphate and the solvent removed by evaporation under reduced pressure to yield a residue of substantially pure 3(2,2-dichlorovinyloxy)benzaldehyde, identification of which was confirmed by infra-red and nuclear magnetic resonance spectroscopy.

I claim:
1. A compound of formula:

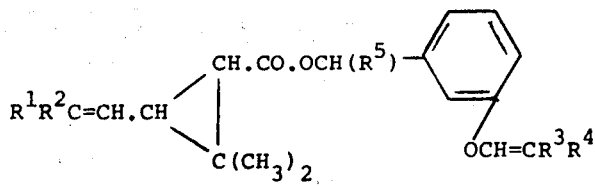

wherein $R^1$ and $R^2$ represent halogen radicals or lower alkyl groups; $R^3$ and $R^4$ represent halogen radicals; and $R^5$ represents a hydrogen atom or the cyano radical.

2. A compound as claimed in claim 1 wherein $R^1$ and $R^2$ are both methyl groups, or both chlorine or both bromine.

3. A compound as claimed in claim 1 wherein $R^3$ and $R^4$ are either both chlorine or both bromine.

4. A compound as claimed in claim 1 wherein $R^1$, $R^2$, $R^3$ and $R^4$ are all chlorine.

5. A compound as claimed in claim 1 in the form of the cis isomer in relation to the substitution of the cyclopropane ring.

6. A compound as claimed in claim 1 in the form of the trans isomer in relation to the substitution pattern of the cyclopropane ring.

7. 3(2,2-Dichlorovinyloxy)benzyl (±) cis/transchrysanthemate.

8. 3(2,2-Dichlorovinyloxy)benzyl (±) cis/trans-2(2,2-dichlorovinyl)3,3-dimethylcyclopropane carboxylate.

9. 3(2,2-Dichlorovinyloxy)benzyl (±) cis-2(2,2-dichlorovinyl)3,3-dimethylcyclopropane carboxylate.

10. 3(2,2-Dichlorovinyloxy)benzyl (±) trans-2(2,2-dichlorovinyl)3,3-dimethylcyclopropane carboxylate.

11. (±)-α-Cyano-3(2,2-dichlorovinyloxy)benzyl (±) cis/trans-2(2,2-dichlorovinyl)3,3-dimethylcyclopropane carboxylate.

12. An insecticidal composition for use in agriculture or horticulture comprising as an active ingredient a compound according to claim 1 in association with an agriculturally or horticulturally acceptable diluent.

13. A method of combating insect pests at an agricultural or horticultural locus which comprises applying to the locus a composition as claimed in claim 12.

14. A compound as claimed in claim 1 wherein $R^1$ and $R^2$ are both chlorine, bromine or methyl, $R^3$ and $R^4$ are both chlorine or bromine and $R^5$ is hydrogen or cyano.

* * * * *

Notice of Adverse Decision in Interference

In Interference No. 99,869, involving Patent No. 3,979,519, N. Punja, INSECTICIDAL ESTERS, final judgment adverse to the patentee was rendered Sept. 3, 1980, as to claim 11.

[*Official Gazette February 24, 1981.*]